(12) United States Patent
Kimura et al.

(10) Patent No.: US 8,097,748 B2
(45) Date of Patent: Jan. 17, 2012

(54) AMORPHOUS COMPOUND AND PRODUCTION METHOD THEREOF

(75) Inventors: Kenji Kimura, Funabashi (JP);
Kazuhiro Kitamura, Osaka (JP);
Hideaki Awa, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/753,552

(22) Filed: Apr. 2, 2010

(65) Prior Publication Data

US 2010/0286316 A1  Nov. 11, 2010

(30) Foreign Application Priority Data

Apr. 6, 2009 (JP) ................................. 2009-091868
Apr. 6, 2009 (JP) ................................. 2009-091869

(51) Int. Cl.
*C07F 9/145* (2006.01)
(52) U.S. Cl. .............................. 558/87; 558/85; 558/177
(58) Field of Classification Search .................. 524/117; 558/85, 87, 177
See application file for complete search history.

(56) References Cited

U.S. PATENT DOCUMENTS

| | | | | |
|---|---|---|---|---|
| 5,830,936 | A * | 11/1998 | Kikuchi et al. | 524/117 |
| 5,889,095 | A * | 3/1999 | Inui et al. | 524/117 |
| 5,914,361 | A * | 6/1999 | Inui et al. | 524/117 |
| 6,846,433 | B2 * | 1/2005 | Okamoto et al. | 252/299.01 |
| 7,635,732 | B2 * | 12/2009 | Kimura et al. | 524/117 |
| 7,683,112 | B2 * | 3/2010 | Kimura et al. | 524/117 |
| 7,820,746 | B2 * | 10/2010 | Soma et al. | 524/117 |
| 2006/0122295 | A1 * | 6/2006 | Oysaed et al. | 524/128 |
| 2009/0280310 | A1 * | 11/2009 | Nitta et al. | 428/220 |

FOREIGN PATENT DOCUMENTS

EP  0 823 435 A2  2/1998

OTHER PUBLICATIONS

DeScamps, M., "Practical Use of Amorphous API's: Features and Stability," The 6th Annual Polymorphism & Crystallisation 2009, Mar. 11-13, 2009, XP-002581540, Slides 23, 25, 28-30, 32-34, London.
Extended European Search Report issued on Jun. 17, 2010 for the corresponding European Patent Application No. EP 10 15 8726.
Hilfiker, R., "Physical Purity of Solids," The 6th Annual Polymorphism & Crystallisation 2009, Mar. 11-12, 2009, XP-002581539, pp. 1-25, London.

* cited by examiner

*Primary Examiner* — Peter Szekely
(74) *Attorney, Agent, or Firm* — Birch, Stewart, Kolasch & Birch LLP (57) ABSTRACT

An amorphous compound of the formula (1):

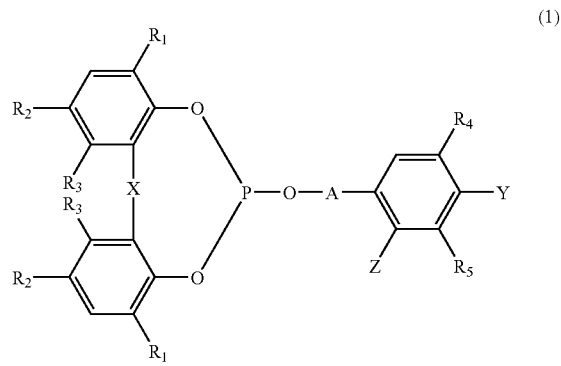

(1)

wherein the temperature showing an endothermic peak by differential scanning calorimetry (DSC) is 40 to 80° C. and the solution rate into n-hexane at 25° C. in the following test system is 1.5 mg/sec or more.
<Test System Regarding Solution Rate>
At 25° C., 1 g of a specimen is charged into a vessel containing 50 g of n-hexane (capacity: 100 ml, outer diameter: 55 mm, height: 70 mm), a 38 mm diameter fan type stirring blade is rotated at a revolution of 100 rpm, and the time until dissolution of the specimen is measured.

2 Claims, 4 Drawing Sheets

AMORPHOUS COMPOUND AND PRODUCTION METHOD THEREOF

TECHNICAL FIELD

The present invention relates to an amorphous compound and a production method thereof.

BACKGROUND ART

A compound of the following formula is known as an active ingredient of a stabilizer for polymers such as thermoplastic polymers (e.g., polybutadiene, etc.) and the like, and it is also known that this compound is obtained in the form of a powdery crystal (see, e.g., patent document 1).

A polymer stabilizer containing the above-described compound as an active ingredient is dissolved in a hydrocarbon solvent, then, compounded, as a dissolved material, in a polymer, to produce a polymer composition.
(Patent document 1) JP-A No. 10-273494

SUMMARY OF THE INVENTION

Active ingredients for a polymer stabilizer are required to have a performance of being dissolved rapidly in a hydrocarbon solvent.

Since a polymer stabilizer containing the above-described compound as an active ingredient is a fine powder, dusting may occur in "handling of the polymer stabilizer" such as a process of preparation of "a dissolved material composed of the polymer stabilizer and a hydrocarbon solvent" used for producing a polymer composition, thus, a polymer stabilizer with which generation of dusting is suppressed is desired.

Under such situation, the present inventors have investigated and resultantly completed the present invention.

That is, the present invention provides the following [1] to [10].

[1]. An amorphous compound of the formula (1):

(wherein, $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R_3$ each independently represents a hydrogen atom or alkyl group having 1 to 8 carbon atoms, X represents a single bond, sulfur atom or —CH($R_6$)— group (here, $R_6$ represents a hydrogen atom, alkyl group having 1 to 8 carbon atoms or cycloalkyl group having 5 to 8 carbon atoms.), A represents an alkylene group having 2 to 8 carbon atoms or *—COR$_7$— group ($R_7$ represents a single bond or alkylene group having 1 to 8 carbon atoms, and * represents bonding to the oxygen side.), either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms.), wherein the temperature showing an endothermic peak by differential scanning calorimetry (DSC) is 40 to 80° C. and the solution rate into n-hexane at 25° C. in the following test system is 1.5 mg/sec or more.

<Test System Regarding Solution Rate>

At 25° C., 1 g of a specimen is charged into a vessel containing 50 g of n-hexane (capacity: 100 ml, outer diameter: 55 mm, height: 70 mm), a 38 mm diameter fan type stirring blade is rotated at a revolution of 100 rpm, and the time until dissolution of the specimen is measured.

[2]. The amorphous compound according to [1], wherein the compound shows a diffraction pattern having two broad peaks of which 2θ at the peak top is present in from 8 to 11° and from 16 to 19°, in an X-ray diffraction pattern in X-ray diffraction measurement using a CuKα spectrum, the ordinate representing a peak intensity and the abscissa representing an angle 2θ of the diffraction line.

[3]. The amorphous compound according to [1], wherein the compound shows a diffraction pattern having two broad peaks of which 2θ at the peak top is present in from 8 to 10° and from 16 to 18°, in an X-ray diffraction pattern in X-ray diffraction measurement using a CuKα spectrum, the ordinate representing a peak intensity and the abscissa representing an angle 2θ of the diffraction line.

[4]. The amorphous compound according to [1], wherein the compound has an atomic arrangement state shown by an X-ray diffraction pattern of FIG. 2, in X-ray diffraction measurement using a CuKα spectrum.

[5]. The amorphous compound according to any one of [1] to [4], wherein in the formula (1), $R_1$, $R_2$ and $R_4$ represent a t-butyl group, $R_3$ represents a hydrogen atom, $R_5$ represents a methyl group, X represents a single bond, A represents a propylene group, Y represents a hydroxyl group and Z represents a hydrogen atom.

[6]. A method of producing an amorphous compound, comprising a first step in which a crystal substance having a melting point of 70 to 220° C. of the formula (1):

(1)

(wherein, $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R_3$ each independently represents a hydrogen atom or alkyl group having 1 to 8 carbon atoms, X represents a single bond, sulfur atom or —CH($R_6$)— group (here, $R_6$ represents a hydrogen atom, alkyl group having 1 to 8 carbon atoms or cycloalkyl group having 5 to 8 carbon atoms.), A represents an alkylene group having 2 to 8 carbon atoms or *—COR$_7$— group ($R_7$ represents a single bond or alkylene group having 1 to 8 carbon atoms, and * represents bonding to the oxygen side.), either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms.)
is melted by heating at a temperature of not lower than the melting point, and a second step in which the melted substance obtained in the first step is cooled and solidified.

[7]. A polymer stabilizer comprising the amorphous compound as described in any one of [1] to [5].

[8]. A polymer composition comprising the polymer stabilizer as described in [7], a hydrocarbon solvent and a polymer.

[9]. A method of producing a polymer composition, comprising a first step in which the polymer stabilizer as described in [7] is dissolved in a hydrocarbon solvent and a second step in which the dissolved substance obtained in the first step is compounded in a polymer.

[10]. The method of producing a polymer composition according to [9], wherein the polymer is a thermoplastic polymer.

EMBODIMENTS FOR CARRYING OUT THE INVENTION

The amorphous compound of the present invention (hereinafter, referred to as the present amorphous compound in some cases) is represented by the formula (1):

(1)

(wherein, $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R_3$ each independently represents a hydrogen atom or alkyl group having 1 to 8 carbon atoms, X represents a single bond, sulfur atom or —CH($R_6$)— group (here, $R_6$ represents a hydrogen atom, alkyl group having 1 to 8 carbon atoms or cycloalkyl group having 5 to 8 carbon atoms.), A represents an alkylene group having 2 to 8 carbon atoms or *—COR$_7$— group ($R_7$ represents a single bond or alkylene group having 1 to 8 carbon atoms, and * represents bonding to the oxygen side.), either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms.)
and the temperature showing an endothermic peak by differential scanning calorimetry (DSC) is 40 to 80° C. and the solution rate into n-hexane at 25° C. in the following test system is 1.5 mg/sec or more.

The polymer stabilizer of the present invention (hereinafter, referred to as the inventive polymer stabilizer in some cases) contains the present amorphous compound.

<Test System Regarding Solution Rate>

At 25° C., 1 g of a specimen is charged into a vessel containing 50 g of n-hexane (capacity: 100 ml, outer diameter: 55 mm, height: 70 mm), a 38 mm diameter fan type stirring blade is rotated at a revolution of 100 rpm, and time until dissolution of the specimen is measured.

In the formula (1), $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group. $R_1$, $R_2$ and $R_4$ represent preferably an alkyl group having 1 to 8 carbon atoms, cycloalkyl group having 5 to 8 carbon atoms or alkylcycloalkyl group having 6 to 12 carbon atoms, and $R_5$ represents preferably a hydrogen atom, alkyl group having 1 to 8 carbon atoms or cycloalkyl group having 5 to 8 carbon atoms.

Here, examples of the alkyl group having 1 to 8 carbon atoms include a methyl group, ethyl group, n-propyl group, i-propyl group, n-butyl group, i-butyl group, sec-butyl group, t-butyl group, t-pentyl group, i-octyl group, t-octyl group and 2-ethylhexyl group. Examples of the cycloalkyl group having 5 to 8 carbon atoms include a cyclopentyl group, cyclohexyl group, cycloheptyl group and cyclooctyl group. Examples of the alkylcycloalkyl group having 6 to 12 carbon atoms include a 1-methylcyclopentyl group, 1-methylcyclohexyl group and 1-methyl-4-i-propylcyclohexyl group. Examples of the aralkyl group having 7 to 12 carbon atoms include a benzyl group, α-methylbenzyl group and α,α-dimethylbenzyl group.

$R_1$ and $R_4$ represent preferably a t-alkyl group such as a t-butyl group, t-pentyl group, t-octyl group and the like, a cyclohexyl group or 1-methylcyclohexyl group, and $R_2$ represents preferably an alkyl group having 1 to 5 carbon atoms such as a methyl group, ethyl group, n-propyl group, i-propyl group, n-butyl group, i-butyl group, sec-butyl group, t-butyl group, t-pentyl group and the like, more preferably a methyl group, t-butyl group or t-pentyl group. $R_5$ represents preferably a hydrogen atom, or an alkyl group having 1 to 5 carbon atoms such as a methyl group, ethyl group, n-propyl group, i-propyl group, n-butyl group, i-butyl group, sec-butyl group, t-butyl group, t-pentyl group and the like.

$R_3$ represents a hydrogen atom or alkyl group having 1 to 8 carbon atoms. As the alkyl group having 1 to 8 carbon atoms represented by $R_3$, alkyl groups as exemplified for $R_1$, $R_2$, $R_4$, $R_5$ and the like are mentioned. $R_3$ represents preferably a hydrogen atom or alkyl group having 1 to 5 carbon atoms, more preferably a hydrogen atom or methyl group.

X represents a single bond, sulfur atom or —CH($R_6$)— group (here, $R_6$ represents a hydrogen atom, alkyl group having 1 to 8 carbon atoms or cycloalkyl group having 5 to 8 carbon atoms.). Here, as the alkyl group having 1 to 8 carbon atoms and the cycloalkyl group having 5 to 8 carbon atoms represented by $R_6$, for example, alkyl groups, cycloalkyl groups and the like as exemplified for $R_1$, $R_2$, $R_4$, $R_5$ are mentioned. X represents preferably a single bond, a methylene group, or a methylene group substituted with a methyl group, ethyl group, n-propyl group, i-propyl group, n-butyl group, i-butyl group, t-butyl group or the like.

A represents an alkylene group having 2 to 8 carbon atoms or *—$COR_7$— group ($R_7$ represents a single bond or alkylene group having 1 to 8 carbon atoms, and * represents bonding to the oxygen side (namely, bonding of a carbonyl to oxygen of a phosphite).). Here, examples of the alkylene group having 2 to 8 carbon atoms include an ethylene group, propylene group, butylene group, pentamethylene group, hexamethylene group, octamethylene group, 2,2-dimethyl-1,3-propylene group and the like, preferably a propylene group. Examples of the alkylene group having 1 to 8 carbon atoms represented by $R_7$ include a methylene group, ethylene group, propylene group, butylene group, pentamethylene group, hexamethylene group, octamethylene group, 2,2-dimethyl-1,3-propylene group and the like. $R_7$ represents preferably a single bond or ethylene group.

Either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms. Here, as the alkyl group having 1 to 8 carbon atoms, for example, alkyl groups as exemplified for $R_1$, $R_2$, $R_4$ and $R_5$ are mentioned. As the alkoxy group having 1 to 8 carbon atoms, for example, alkoxy groups having the same alkyl portion as that of the alkyl group having 1 to 8 carbon atoms as exemplified for $R_1$, $R_2$, $R_4$ and $R_5$ and the like are mentioned. As the aralkyloxy group having 7 to 12 carbon atoms, for example, aralkyloxy groups having the same alkyl portion as that of the alkyl group having 1 to 8 carbon atoms as exemplified for $R_1$, $R_2$, $R_4$ and $R_5$ and the like are mentioned.

Examples of the present amorphous compound include 6-[3-(3-t-butyl-4-hydroxy-5-methylphenyl)propoxy]-2,4,8,10-tetra-t-butyldibenz[d,f][1,3,2]dioxaphosphepin, 6-[3-(3,5-di-t-butyl-4-hydroxyphenyl)propoxy]-2,4,8,10-tetra-t-butyldibenz[d,f][1,3,2]dioxaphosphepin, 6-[3-(3,5-di-t-butyl-4-hydroxyphenyl)propoxy]-4,8-di-t-butyl-2,10-dimethyl-12H-dibenz[d,g][1,3,2]dioxaphosphocin, 6-[3-(3,5-di-t-butyl-4-hydroxyphenyl)propionyloxy]-4,8-di-t-butyl-2,10-dimethyl-12H-dibenz[d,g][1,3,2]dioxaphosphocin and the like.

The present amorphous compound includes, preferably, 6-[3-(3-t-butyl-4-hydroxy-5-methylphenyl)propoxy]-2,4,8,10-tetra-t-butyldibenz[d,f][1,3,2]dioxaphosphepin, that is, a substance of the formula (1) in which $R_1$, $R_2$ and $R_4$ represent a t-butyl group, $R_3$ and Z represent a hydrogen atom, $R_5$ represents a methyl group, A represents a propylene group, X represents a single bond and Y represents a hydroxy group, 6-[3-(3,5-di-t-butyl-4-hydroxyphenyl)propoxy]-2,4,8,10-tetra-t-butyldibenz[d,f][1,3,2]dioxaphosphepin, that is, a substance of the formula (1) in which $R_1$, $R_2$, $R_4$ and $R_5$ represent a t-butyl group, $R_3$ and Z represent a hydrogen atom, A represents a propylene group, X represents a single bond and Y represents a hydroxy group, and the like. The present amorphous compound includes, more preferably, 6-[3-(3-t-butyl-4-hydroxy-5-methylphenyl)propoxy]-2,4,8,10-tetra-t-butyldibenz[d,f][1,3,2]dioxaphosphepin.

In the present amorphous compound, the temperature showing an endothermic peak by differential scanning calorimetry (DSC) is 40 to 80° C. In the present amorphous compound, the solution rate is preferably 1.5 mg/sec or more and 9 mg/sec or less, more preferably 3 mg/sec or more and 8 mg/sec or less, in "Test system regarding solution rate" in which, at 25° C., 1 g of a specimen is charged into a vessel containing 50 g of n-hexane (capacity: 100 ml, outer diameter: 55 mm, height: 70 mm), a 38 mm diameter fan type stirring blade is rotated at a revolution of 100 rpm, and time until dissolution of the specimen is measured. In the present invention, "until dissolution of a specimen" means "until incapability of visual confirmation of solid dispersion of a specimen".

Figure 2:
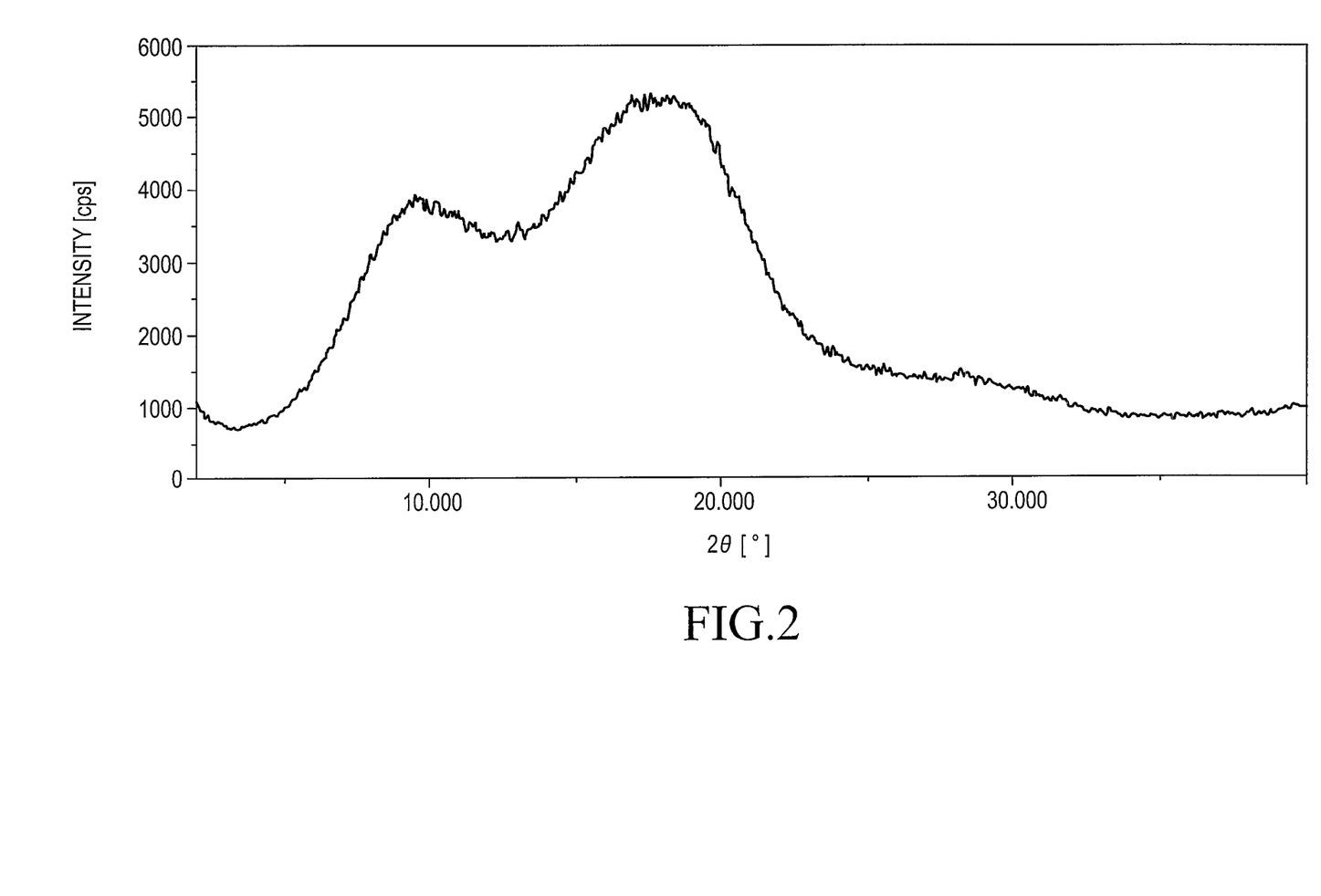
FIG. 2 is a view showing an X-ray diffraction pattern in X-ray diffraction measurement using a CuKα spectrum. Since this pattern contains a broad peak, an amorphous atomic arrangement state can be confirmed.

The present amorphous compound includes, for example, substances having an atomic arrangement state shown by the X-ray diffraction pattern in FIG. 2 in X-ray diffraction measurement using a CuKα spectrum, and the like.

FIG. 2 shows a result of X-ray diffraction measurement in which the ordinate represents a peak intensity and the abscissa represents an angle 2θ of the diffraction line, and examples of the present amorphous compound include preferably amorphous substances showing a diffraction pattern having two broad peaks of which 2θ at the peak top is present in from 8 to 11° and from 16 to 19°. More preferably mentioned are amorphous substances showing a diffraction pattern having two broad peaks of which 2θ at the peak top is present in from 8 to 10° and from 16 to 18°. The term "broad peak" means that the base of the peak has a minimum width of at least 8° on the 2θ axis.

Examples of the shape of the present amorphous compound include plate, fine powder, pellet, granule, tablet, approximate sphere, approximate hemisphere, flake and the like, preferably approximate sphere or approximate hemisphere. The size of the present amorphous compound is not particularly restricted, and its particle size is, for example, about 1 mm to about 6 mm, or the like, preferably about 2 mm to about 5 mm, and its height is, for example, about 1 mm to about 4 mm, or the like, preferably about 1 mm to about 3 mm. The weight per one particle of the present amorphous compound is not particularly restricted, and it is, for example, about 1 mg to about 25 mg. The hardness of the present amorphous compound is not particularly restricted, and it is, for example, about 10 N to about 30 N.

When the shape of the present amorphous compound is plate, it can also be pulverized to give flakes, if necessary.

As the method of producing the present amorphous compound, there is mentioned, for example, a production method comprising a first step in which a crystal substance having a melting point of 70 to 220° C., preferably 100 to 140° C. of the formula (1):

(wherein, $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R_3$ each independently represents a hydrogen atom or alkyl group having 1 to 8 carbon atoms, X represents a single bond, sulfur atom or —CH($R_6$)— group (here, $R_6$ represents a hydrogen atom, alkyl group having 1 to 8 carbon atoms or cycloalkyl group having 5 to 8 carbon atoms.), A represents an alkylene group having 2 to 8 carbon atoms or *—COR$_7$— group ($R_7$ represents a single bond or alkylene group having 1 to 8 carbon atoms, and * represents bonding to the oxygen side.), either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms.)
is melted by heating at a temperature of not lower than the melting point, and a second step in which the melted substance obtained in the first step is cooled and solidified.

In the first step of the production method of the present amorphous compound, the above-described crystal substance may be melted by heating at a temperature of not lower than the melting point, and "temperature of not lower than the melting point" means a temperature of, for example, from about 120° C. to about 270° C., or the like, preferably, from about 130° C. to about 230° C., or the like.

In the second step of the production method of the present amorphous compound, the melted substance obtained in the first step may be cooled and solidified, and the temperature and the time of "cooling" include, for example, a temperature of about 50° C. or lower and a time of about 10 seconds or more, preferably a temperature of from about 0° C. to about 40° C. and a time of about 15 seconds or more and about 2 minutes or less, more preferably a temperature of from about 10° C. to about 30° C. and a time of from about 15 seconds to about 1 minute.

Examples of the method of cooling and solidifying the melted substance obtained in the first step include a method in which the melted substance obtained in the first step is sprayed or dropped on a cooled heat exchange plate (for example, a sheet made of a metal such as stainless steel, and the like), a method in which the melted substance obtained in the first step is dropped into cooled water or poor solvent, a method in which the melted substance obtained in the first step is continuously extruded onto a cooled belt, and the like.

Examples of the method of dropping a melted substance include a method of dropping from a dropping tube, specifically, a method in which a melted substance is filled in a rolldrop mode granulator, rotoform mode granulator or the like before dropping.

Here, the rolldrop mode granulator is usually a granulator having a rotation drum with a projection and having a mechanism in which a melted substance is scraped by the leading edge of the projection, and the melted substance is dropped onto a heat exchange plate by the action of centrifugal force obtained by rotation of the rotation drum and/or gravity force.

The rotoform mode granulator is usually a granulator having a cylindrical part, the cylindrical part having a pore through which a melted substance is received into the inside of the cylindrical part, and having a mechanism in which the melted substance is dropped from the pore onto a heat exchange plate.

In particular, dropping by the rotoform mode granulator is preferable.

For adjusting the weight per one drop of the inventive amorphous compound to a desired value in the method of dropping a melted substance from a dropping tube, it may be permissible that the amount of dropping of the melted substance from a dropping tube is controlled by regulating the aperture of the dropping tube, the viscosity of the melted substance, and the like. Specifically, in the case of the rolldrop mode granulator, it may be permissible the amount of the melted substance scraped by the leading edge of a projection is controlled, and in the case of the rotoform mode granulator, it may be permissible that the amount of dropping of the melted substance from a dropping tube is controlled by regulating the size of the pore, the viscosity of the melted substance, and the like.

"The cooled heat exchange plate" includes, for example, a heat exchange plate of about 0° C. to about 50° C. Specifically mentioned are a stainless steel belt controlled to given temperature with water and the like, a stainless steel belt controlled to given temperature with cold air and the like, a stainless steel plate controlled to given temperature with water and the like, a stainless steel plate controlled to given temperature with cold air and the like. It is preferable that the plane of the heat exchange plate onto which a melted substance is dropped is smooth.

The content of the present amorphous compound in the inventive polymer stabilizer is usually about 1 wt % or more, preferably about 75 wt % or more, more preferably about 85 wt % or more and further more preferably about 95 wt % or more, with respect to the total amount of the inventive polymer stabilizer. The inventive polymer stabilizer may have a content of the present amorphous compound of 100 wt %.

The inventive polymer stabilizer may contain various additives in a range not disturbing the effect of the present invention.

Examples of such additives include phenol antioxidants such as n-octadecyl-3-(4-hydroxy-3,5-di-t-butylphenyl)propionate (melting point 50 to 55° C.), 2,6-di-t-butyl-4-methylphenol (melting point 69° C. (coagulation point)), 2,2-thiodiethylene-bis-[3-(3,5-di-t-butyl-4-hydroxyphenyl) propionate] (melting point 63° C. or higher), tri-ethylene glycol-bis-[3-(3-t-butyl-5-methyl-4-hydroxyphenyl)propionate] (melting point 76 to 79° C.), 3,9-bis[2-{3-(3-t-butyl-4-hydroxy-5-methylphenyl)propionyloxy}-1,1-dimethylethyl]-2,4,8,10-tetraoxaspiro[5·5]undecane (melting point 110 to 130° C.), pentaerythrityl tetrakis{3-(3,5-di-t-butyl-4-hydroxyphenyl)-propionate} (melting point 110 to 130° C.), 2-t-butyl-6-(3-t-butyl-2-hydroxy-5-methylbenzyl)-4-methylphenyl acrylate (melting point 130° C. or higher), 2-[1-(2-hydroxy-3,5-di-t-pentylphenyl)ethyl]-4,6-di-t-pentylphenyl acrylate (melting point 119° C.), 1,3,5-trimethyl-2,4,6-tris(3, 5-di-t-butyl-4-hydroxybenzyl)benzene (melting point 240 to 245° C.), tris(3,5-di-t-butyl-4-hydroxybenzyl) isocyanurate (melting point 218 to 223° C.), 1,3,5-tris(4-t-butyl-3-hydroxy-2,6-dimethylbenzyl)-1,3,5-triazine-2,4,6-(1H,3H, 5H)-trione (melting point 159 to 162° C.), 2,2'-methylenebis (6-t-butyl-4-methylphenol) (melting point 128° C. or higher), 4,4'-butylidenebis(6-t-butyl-3-methylphenol) (melting point 209° C. or higher), 4,4'-thiobis(6-t-butyl-3-methylphenol) (melting point 160° C. or higher) and the like, sulfur antioxidants, such as di-n-dodecyl 3,3'-thiodipropionate (melting point 40 to 42° C.), di-n-tetradecyl 3,3'-thiodipropionate (melting point 49 to 54° C.), di-n-octadecyl 3,3'-thiodipropionate (melting point 65 to 67° C.), pentaerythrityl tetrakis(3-dodecylthiopropionate) (melting point about 46° C.) and the like, phosphorus antioxidants, such as tris(2,4-di-t-butylphenyl) phosphite (melting point 183 to 187° C.), bis(2,4-di-t-butylphenyl)pentaerythritol diphosphite (melting point 160 to 180° C.), bis(2,6-di-t-butyl-4-methylphenyl)pentaerythritol diphosphite (melting point 237 to 238° C.), bis(2,4-dicumylphenyl)pentaerythritol diphosphite (melting point 221 to 230° C.), tetrakis(2,4-di-t-butylphenyl)-4,4'-biphenylene diphosphonite (melting point 75 to 90° C.), bis[2,4-di-t-butyl (6-methyl)phenyl]ethyl phosphite (melting point 89 to 92° C.) and the like, hindered amine antioxidants, such as bis(2,2,6,6-tetramethyl-4-piperidyl) sebacate (melting point 81 to 86° C.), 2,2, 6,6-tetramethyl-4-piperidyl methacrylate (melting point 58° C.), poly[{6-(1,1,3,3,-tetramethylbutyl)amino-1,3,5-triazine-2,4-diyl}{(2,2,6,6-tetramethyl-4-piperidyl)imino}-1,6-hexamethylene{(2,2,6,6-tetramethyl-4-piperidyl)imino}] (melting point 100 to 135° C.) and the like, ultraviolet absorbers, such as 2-hydroxy-4-n-octyloxy benzophenone (melting point 45° C. or higher), 2-(2H-benzotriazol-2-yl)-4,6-di-t-pentyl phenol (melting point 77° C. or higher), 2-[4,6-bis(2,4-dimethylphenyl)-1,3,5-triazin-2-yl]-5-(octyloxy)phenol (melting point 87 to 89° C.), 2-(2-hydroxy-5-methylphenyl)benzotriazole (melting point 127° C.), 2-(3-t-butyl-2-hydroxy-5-methylphenyl)-5-chlorobenzotriazole (melting point 137° C.), 2,4-di-t-butylphenyl 3,5-di-t-butyl-4-hydroxybenzoate (melting point 192° C.) and the like, nucleating agents, such as Na salt of α-naphthalenesulfonic acid, Mg salt of α-naphthalenesulfonic acid, Ca salt of α-naphthalenesulfonic acid, Al salt of α-naphthalenesulfonic acid, Na salt of 8-amino-naphthalenesulfonic acid, Na salt of benzenesulfonic acid, Mg salt of benzenesulfonic acid, Ca salt of benzenesulfonic acid, Al salt of benzenesulfonic acid, Ca salt of 2,5-dichlorobenzenesulfonic acid, Mg salt of 2,5-dichlorobenzenesulfonic acid, Ca salt of m-xylenesulfonic acid, Mg salt of m-xylenesulfonic acid, benzoic acid (melting point 122° C.), p-isopropylbenzoic acid, o-t-butylbenzoic acid, p-t-butylbenzoic acid, monophenylacetic acid (melting point 77° C.), diphenylacetic acid, Li salt of diphenylacetic acid, Na salt of diphenylacetic acid, Mg salt of diphenylacetic acid, Ca salt of diphenylacetic acid, Ba salt of diphenylacetic acid, Al salt of diphenylacetic acid, phenyldimethylacetic acid, Li salt of phenyldimethylacetic acid, Na salt of phenyldimethylacetic acid, Mg salt of phenyldimethylacetic acid, Ca salt of phenyldimethylacetic acid, Ba salt of phenyldimethylacetic acid, Mg salt of phthalic acid, succinic acid (melting point 185° C.), Li salt of succinic acid, Na salt of succinic acid, Mg salt of succinic acid, Ca salt of succinic acid, Ba salt of succinic acid, glutaric acid (melting point 95 to 99° C.), Li salt of glutaric acid, Na salt of glutaric acid, Mg salt of glutaric acid, Ca salt of glutaric acid, Ba salt of glutaric acid, adipic acid (melting point 151 to 153° C.), suberic acid, Li salt of suberic acid, Na salt of suberic acid, Mg salt of suberic acid, Ca salt of suberic acid, Ba salt of suberic acid, sebacic acid, Li salt of sebacic acid, Na salt of sebacic acid, Mg salt of sebacic acid, Ca salt of sebacic acid, Al salt of sebacic acid, diphenylphosphinic acid (melting point 193 to 196° C.), Li salt of diphenylphosphinic acid, Na salt of diphenylphosphinic acid, K salt of diphenylphosphinic acid, Ca salt of diphenylphosphinic acid, Mg salt of diphenylphosphinic acid, Al salt of diphenylphosphinic acid, Li salt of 4,4'-dichlorodiphenylphosphinic acid, Na salt of 4,4'-dimethyldiphenylphosphinic acid, dinaphthylphosphinic acid, Li salt of dinaphthylphosphinic acid, Na salt of dinaphthylphosphinic acid, Mg salt of dinaphthylphosphinic acid, Ca salt of dinaphthylphosphinic acid, Al salt of dinaphthylphosphinic acid, and the like, metal soaps containing fatty acid metal salts such as calcium stearate, hydrotalcite, inorganic or organic anti-blocking agents, such as aluminum silicate, synthetic silica, natural silica, zeolite, kaolin, diatomaceous earth and the like, pigments, such as carbon black, titanium oxide, phthalocyanine pigment, quinacridone pigment, isoindolinone pigment, perylene or perylene pigment, quinophthalone pigment, diketopyrrolo-pyrrole pigment, dioxazine pigment, disazo-condensation pigment, benzimidazolone pigment and the like, flame retardants, such as decabromobiphenyl, antimony trioxide, phosphorus-based flame retardant, aluminum hydroxide, and the like, antistatic agents, such as quaternary ammonium salt type cationic surfactant, betaine type ampholytic surfactant, alkyl phosphate type anionic surfactant; cationic surfactant such as primary amine salt, secondary amine salt, tertiary amine salt, quaternary amine salt, pyridine derivative and the like; anionic surfactant such as sulfated oil, soap, sulfated ester oil, sulfated amide oil, olefin sulfated ester salts, fatty alcohol sulfate ester salts, alkyl sulfate ester salt, fatty acid ethylsulfonate salt, alkylnaphthalenesulfonate salt, alkylbenzenesulfonate salt, succinate ester sulfonate salt, phosphate ester salt and the like; nonionic surfactant such as polyhydric alcohol partial fatty acid ester, fatty alcohol ethylene oxide adduct, fatty acid ethylene oxide adduct, fatty amino or fatty acid amide ethylene oxide adduct, alkylphenol ethylene oxide adduct, polyhydric alcohol partial fatty acid ester ethylene oxide adduct, polyethylene glycol, and the like; ampholytic surfactants such as carboxylic acid derivative, imidazoline derivative and the like.

Lubricants, fillers, plasticizers, processing aids, foaming agents, emulsifiers, gloss agents, binders and the like may also be contained in the inventive polymer stabilizer.

The content of various additives in the inventive polymer stabilizer is usually about 25 wt % or less, preferably about 15 wt % or less, more preferably about 5 wt % or less, with respect to the total amount of the inventive polymer stabilizer.

The polymer composition of the present invention (hereinafter, referred to as present polymer composition in some cases) contains the inventive polymer stabilizer, a hydrocarbon solvent and a polymer.

Examples of the production method of the present polymer composition include (1) a production method containing a first step in which the inventive polymer stabilizer is dissolved in a hydrocarbon solvent, and a second step in which the dissolved substance obtained in the first step is compounded into a polymer, (2) a production method containing a step of melt-kneading the inventive polymer stabilizer and a polymer, and other methods.

Examples of the hydrocarbon solvent to be used in the first step of the above-described production method (1) include hydrocarbon solvents such as pentane, hexane, cyclopentane, cyclohexane and the like.

The mixing ratio of the inventive polymer stabilizer and a hydrocarbon solvent in the first step is not particularly restricted providing the inventive polymer stabilizer is dissolved in the hydrocarbon solvent, and for example, the inventive polymer stabilizer is contained in a ratio of 10 to 90 wt % with respect to the total amount of the inventive polymer stabilizer and the hydrocarbon solvent.

Also the mixing method thereof is not particularly restricted, and for example, a method in which the inventive polymer stabilizer is added to a hydrocarbon solvent stored in a vessel under a nitrogen atmosphere and mixed by stirring at about −10 to 70° C., a method in which a hydrocarbon solvent is added to the inventive polymer stabilizer stored in a vessel under a nitrogen atmosphere and mixed by stirring at about −10 to 70° C., and other methods, are mentioned.

Regarding the compounding ratio of the inventive polymer stabilizer and a polymer in the second step of the above-described production method (1) and in the step of the above-described production method (2), the inventive polymer stabilizer is compounded so that it is usually 2 parts by weight or less, preferably 0.01 part by weight or more and 2 parts by weight or less, more preferably 0.01 part by weight or more and 1 part by weight or less, with respect to 100 parts by weight of the polymer.

In the production method of the present polymer composition, it is preferable that the polymer is a thermoplastic polymer.

Here, the thermoplastic polymer is not particularly restricted providing it is a commercially available resin, and examples thereof include polypropylene resin such as ethylene-propylene copolymer and the like; polyethylene resin (high density polyethylene (HD-PE), low density polyethylene (LD-PE), linear low density polyethylene (LLDPE) and the like), methylpentene polymer, ethylene-ethyl acrylate copolymer, ethylene-vinyl acetate copolymer; polystyrenes (polystyrene such as poly(p-methylstyrene), poly(α-methylstyrene) and the like; acrylonitrile-styrene copolymer, acrylonitrile-butadiene-styrene copolymer, special acrylic rubber-acrylonitrile-styrene copolymer, acrylonitrile-chlorinated polyethylene-styrene copolymer, styrene-butadiene copolymer and the like), chlorinated polyethylene, polychloroprene, chlorinated rubber, polyvinyl chloride, polyvinylidene chloride, methacrylic resin, ethylene-vinyl alcohol copolymer, fluorine resin, polyacetal, grafted polyphenylene ether resin, polyphenylene sulfide resin, polyurethane, polyamide, polyester resin (for example, polyethylene terephthalate, polybutylene terephthalate and the like), polycarbonate, polyacrylate, polysulfone, polyether ether ketone, polyether sulfone, aromatic polyester resin, diallyl phthalate prepolymer, silicone resin, 1,2-polybutadiene, polyisoprene, butadiene/acrylonitrile copolymer, ethylene-methyl methacrylate copolymer, and the like, and particularly, preferable from the standpoint of good molding processability are polyethylene resin, polypropylene resin and polystyrenes.

Here, the polypropylene resin means a polyolefin containing a structural unit derived from propylene, and specifically mentioned are crystalline propylene homopolymers, propylene-ethylene random copolymers, propylene-α-olefin random copolymers, propylene-ethylene-α-olefin copolymers; polypropylene block copolymers composed of a propylene homopolymer component or a copolymer component mainly composed of propylene, and a copolymer component of propylene and ethylene and/or α-olefin; and the like.

In the case of use of polypropylene resins as the thermoplastic polymer in the present invention, the polypropylene resins may be used singly or two or more of them may be blended and used.

The α-olefin is, for example, an α-olefin having 4 to 12 carbon atoms, and examples thereof include 1-butene, 1-pentene, 1-hexene, 4-methyl-1-pentene, 1-octene, 1-decene and the like, preferably 1-butene, 1-hexene and 1-octene.

Examples of the propylene-α-olefin random copolymer include propylene-1-butene random copolymer, propylene-1-hexene random copolymer, propylene-1-octene random copolymer and the like.

Examples of the propylene-ethylene-α-olefin copolymer include propylene-ethylene-1-butene copolymer, propylene-ethylene-1-hexene copolymer, propylene-ethylene-1-octene copolymer and the like.

In the polypropylene block copolymers composed of a propylene homopolymer component or a copolymer component mainly composed of propylene, and a copolymer component of propylene and ethylene and/or α-olefin, examples of the copolymer component mainly composed of propylene include a propylene-ethylene copolymer component, propylene-1-butene copolymer component, propylene-1-hexene copolymer component and the like, and examples of the copolymer component of propylene and ethylene and/or α-olefin include a propylene-ethylene copolymer component, propylene-ethylene-1-butene copolymer component, propylene-ethylene-1-hexene copolymer component, propylene-ethylene-1-octene copolymer component, propylene-1-butene copolymer component, propylene-1-hexene copolymer component, propylene-1-octene copolymer component and the like. The content of ethylene and/or α-olefin having 4 to 12 carbon atoms in the copolymer component of propylene and ethylene and/or α-olefin is usually 0.01 to 20 wt %.

Examples of the polypropylene block copolymers composed of a propylene homopolymer component or a copolymer component mainly composed of propylene, and a copolymer component of propylene and ethylene and/or α-olefin include a propylene-ethylene block copolymer, (propylene)-(propylene-ethylene) block copolymer, (propylene)-(propylene-ethylene-1-butene) block copolymer, (propylene)-(propylene-ethylene-1-hexene) block copolymer, (propylene)-(propylene-1-butene) block copolymer, (propylene)-(propylene-1-hexene) block copolymer, (propylene-ethylene)-(propylene-ethylene-1-butene) block copolymer, (propylene-ethylene)-(propylene-ethylene-1-hexene) block copolymer, (propylene-ethylene)-(propylene-1-butene) block copolymer, (propylene-ethylene)-(propylene-1-hexene) block copolymer, (propylene-1-butene)-(propylene-ethylene) block copolymer, (propylene-1-butene)-(propylene-ethylene-1-butene) block copolymer, (propylene-1-butene)-

(propylene-ethylene-1-hexene) block copolymer, (propylene-1-butene)-(propylene-1-butene) block copolymer, (propylene-1-butene)-(propylene-1-hexene) block copolymer and the like.

In the case of use of a polypropylene resin as the thermoplastic polymer in the present invention, preferable is a polypropylene block copolymers composed of a crystalline propylene homopolymer, a propylene homopolymer component or a copolymer component mainly composed of propylene, and a copolymer component of propylene and ethylene and/or α-olefin having 4 to 12 carbon atoms. More preferable is a polypropylene block copolymers composed of a propylene homopolymer component or a copolymer component mainly composed of propylene, and a copolymer component of propylene and ethylene and/or α-olefin having 4 to 12 carbon atoms.

EXAMPLES

The present invention will be illustrated further in detail below by examples and comparative examples.

As the crystal substance having melting point of 70 to 220° C. of the formula (1), 6-[3-(3-t-butyl-4-hydroxy-5-methylphenyl)propoxy]-2,4,8,10-tetra-t-butyldibenzo[d,f][1,3,2]dioxaphosphepin (melting point 115 to 125° C., manufactured by Sumitomo Chemical Co., Ltd.) (hereinafter, referred to as compound (1) in some cases.) was used.

Example 1

A compound (1) was put into a melting tank heated at 200° C., and melted. Then, the resultant melted substance was dropped on a stainless steel plate cooled with cooling water of 30° C., then, cooled and solidified for 22 seconds on the stainless steel plate, thereby obtaining an approximately hemi-spherical amorphous compound. The resultant amorphous compound had a particle size (width) of 2.8 mm and a height of 1.9 mm.

Next, the resultant amorphous compound was subjected to the following DSC analysis, XRD analysis and solution rate measurement, and the like.
(DSC Analysis)

The resultant amorphous compound was sealed in an aluminum cell, using a differential scanning calorimeter DSC-60A manufactured by Shimadzu Corp. The aluminum cell was inserted into a sample holder equipped to the above-described differential scanning calorimeter, then, an endothermic pattern was observed while heating the sample holder under a nitrogen atmosphere at a rate of 5° C./min up to 200° C.

Figure 1:
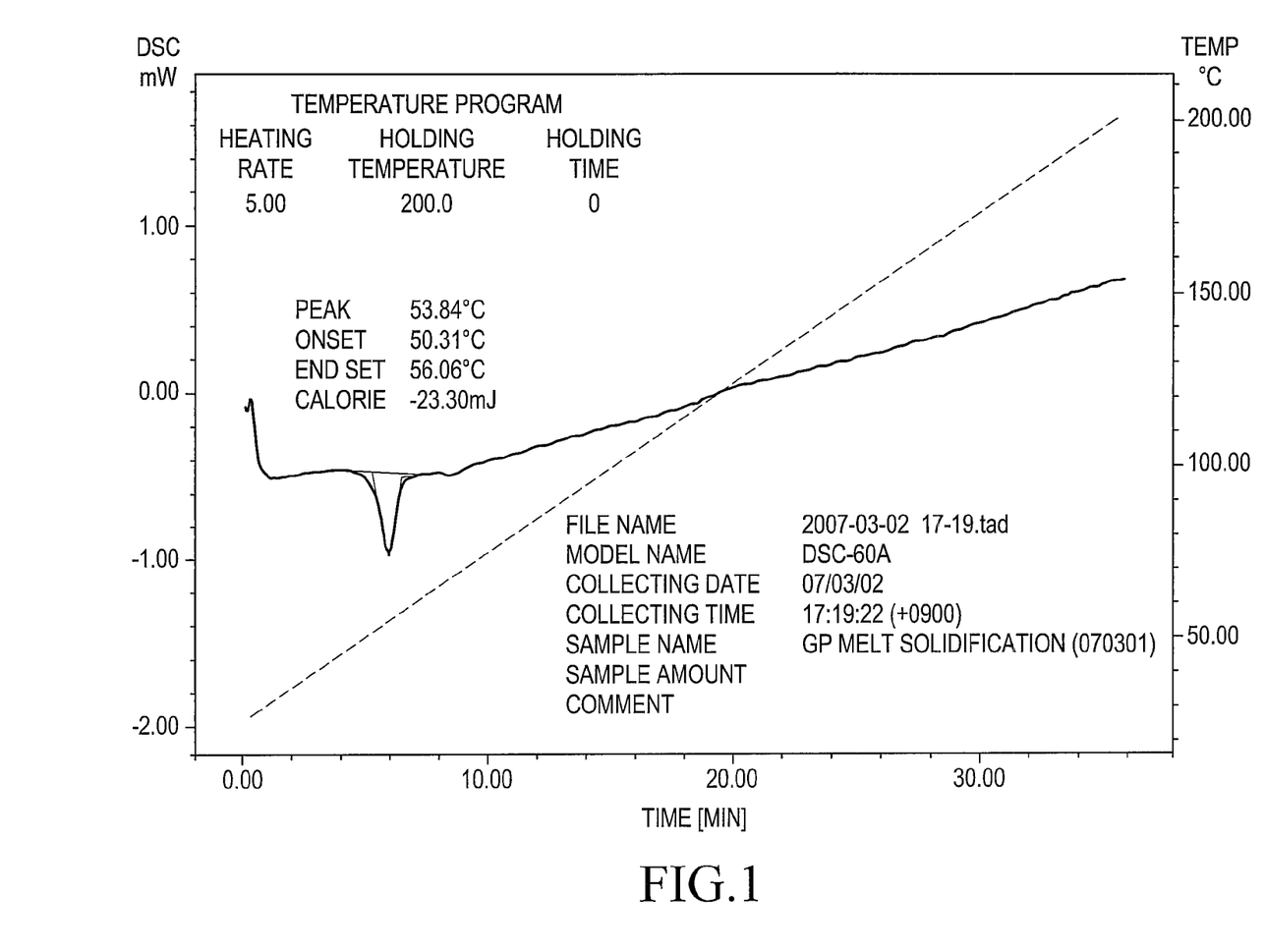
FIG. 1 is a view showing an endothermic pattern in differential scanning calorimetry using DSC. It is a view showing an amorphous atomic arrangement state since this pattern contains a broad peak in phase transition.

As a result, the endothermic peak of the resultant amorphous compound was 53.84° C., as shown in FIG. 1.
(XRD Analysis)

The resultant amorphous compound was pulverized. Then, the resultant pulverized substance was inserted into a sample holder equipped to RINT2000 vertical goniometer manufactured by Rigaku Corporation, then, an X-ray diffraction pattern in X-ray diffraction measurement was measured using a CuKα spectrum. The resultant X-ray diffraction pattern was shown in FIG. 2.

As a result, an amorphous atomic arrangement state could be confirmed since the pattern contained broad peaks, as shown in FIG. 2.
(Measurement of Particle Size (Width) and Height of Granular Amorphous Compound)

The particle size (width) and height of the resultant amorphous compound were measured using a vernier caliper. The measurement was repeated 10 times, and the average values thereof were used as "particle size (width) of granular amorphous compound" and "height of granular amorphous compound".
(Measurement of Solution Rate)

At 25° C., 1 g of a specimen was charged into a vessel containing 50 g of n-hexane (capacity: 100 ml, outer diameter: 55 mm, height: 70 mm), a 38 mm diameter fan type stirring blade was rotated at a revolution of 100 rpm, and the time until dissolution of the above-described specimen was measured. The results were shown in Table 1 as solution rate in terms of "mg/sec" unit.

Comparative Example 1

A compound (1) was subjected to DSC analysis, XRD analysis and solution rate measurement, and the like according to the same manners as described above excepting that the "compound (1)" itself was used instead of the "resultant amorphous compound".

Figure 3:
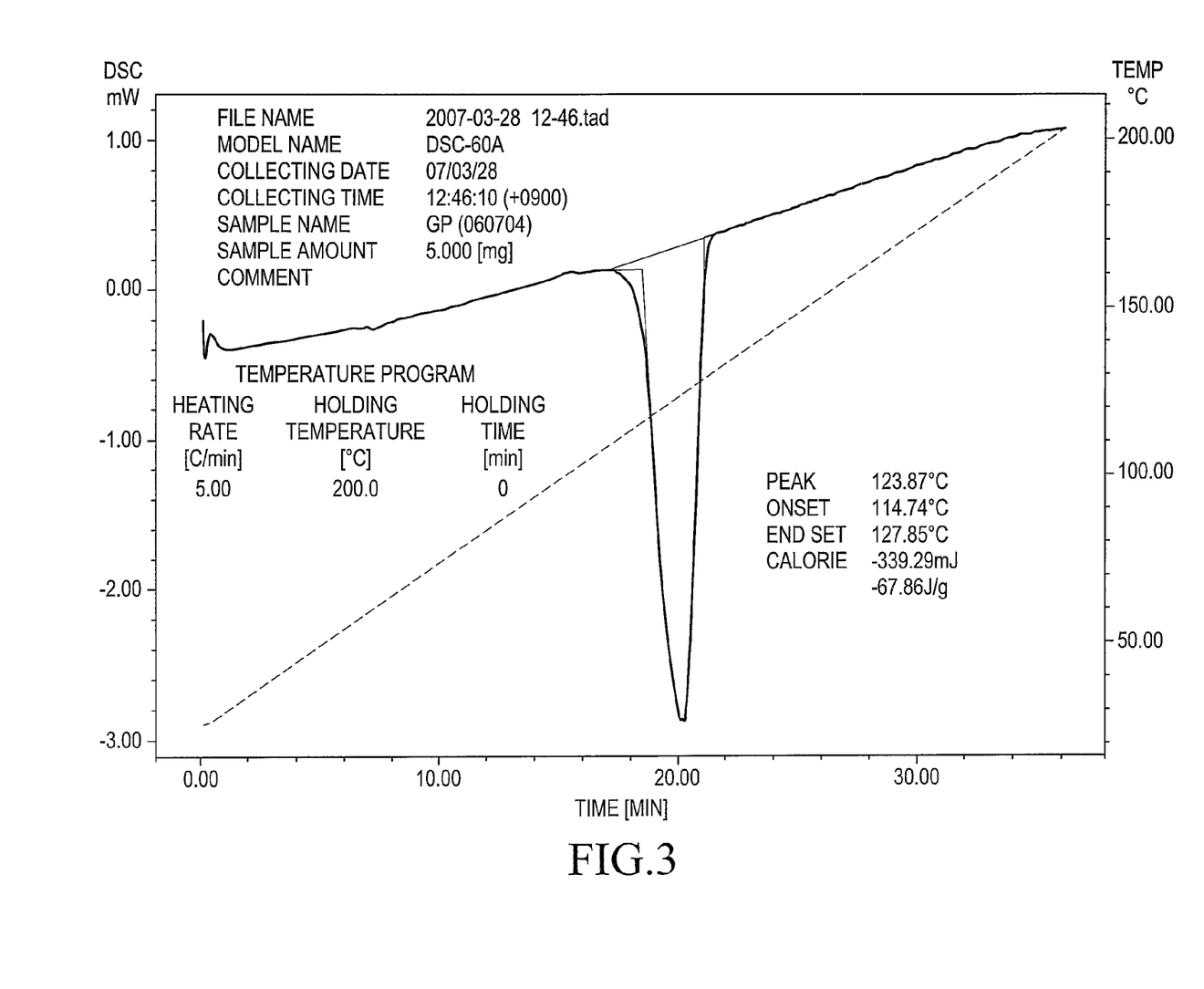
FIG. 3 is a view showing an endothermic pattern in differential scanning calorimetry using DSC. It is a view showing a crystalline atomic arrangement state since this pattern contains one point sharp peak at the melting point.
Figure 4:
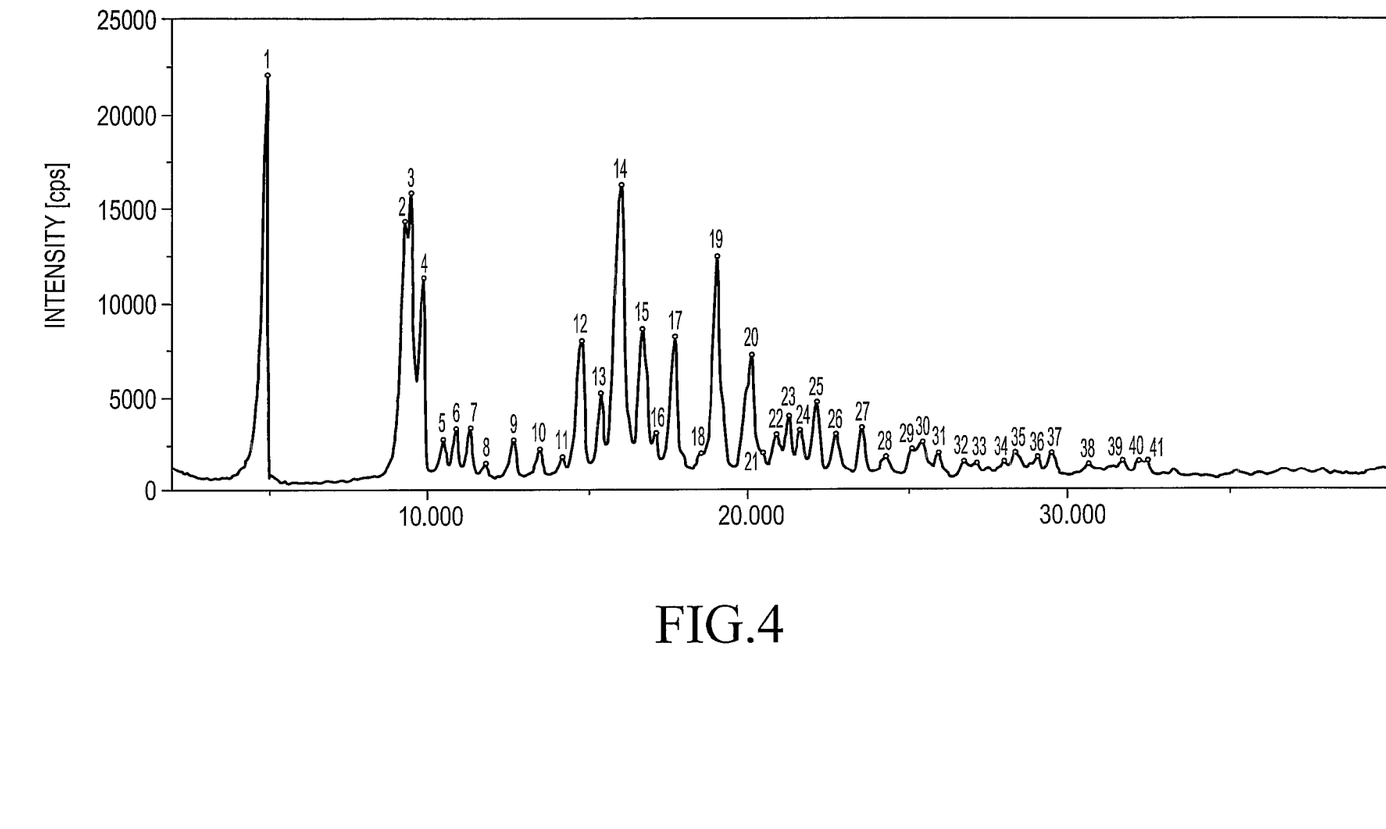
FIG. 4 is a view showing an X-ray diffraction pattern in X-ray diffraction measurement using a CuKα spectrum. It is a view showing a crystalline atomic arrangement state, since this pattern contains a sharp diffraction peak at each crystal lattice plane.

The results were shown in FIG. 3 (DSC analysis) and FIG. 4 (XRD analysis) and Table 1 (particle size (width) and height, solution rate).

TABLE 1

|  | Active ingredient of specimen | Particle size/ height (mm) | Solution rate (mg/sec) |
| --- | --- | --- | --- |
| Example 1 | Present amorphous | 3.4/2.2 | 7.123 |
| Comparative Example 1 | Crystal substance compound (1) | White fine particle | 0.744 |

Example 2

A polymer stabilizer was prepared in which the content of the amorphous compound obtained in Example 1 (approximately hemi-spherical amorphous compound) was 100 wt % with respect to the total weight. This polymer stabilizer was mixed in an amount of 10 parts by weight with each 100 parts by weight of four hydrocarbon solvents: pentane, hexane, cyclopentane and cyclohexane, and the mixtures were stirred at a solvent temperature of 25° C. to attain dissolution thereof. In the operation, the condition of dusting generated from the polymer stabilizer was observed, however, no generation of dusting was confirmed in use of any of the hydrocarbon solvents. Next, the resultant dissolved substance was compounded with polypropylene as a thermoplastic polymer, so that the amount of the polymer stabilizer was 0.5 parts by weight with respect to 100 parts by weight of the thermoplastic polymer, thereby producing a polymer composition.

Comparative Example 2

A polymer composition was produced in the same manner as in Example 2, using a polymer stabilizer based on the specimen used in Comparative Example 1. This polymer stabilizer was mixed in an amount of 10 parts by weight with each 100 parts by weight of four hydrocarbon solvents: pentane, hexane, cyclopentane and cyclohexane, and the mixtures were stirred at a solvent temperature of 25° C. to attain dissolution thereof. In the operation, the condition of dusting generated from the polymer stabilizer was observed, as a result, generation of dusting was confirmed in use of any of the hydrocarbon solvents.

TABLE 2

| | Generation of dusting | Polymer stabilizing effect | remarks |
|---|---|---|---|
| Example 2 | none | positive | Inventive polymer stabilizer |
| Comparative Example 2 | positive | positive | Comparative polymer stabilizer |

INDUSTRIAL APPLICABILITY

The amorphous compound of the present invention has an excellent performance of dissolving quickly in a hydrocarbon solvent, and thus is extremely useful as an active ingredient of a polymer stabilizer.

The polymer stabilizer of the present invention manifests no dusting, and thus is excellent as a stabilizer for polymers.

The invention claimed is:

1. A method of producing an amorphous compound, comprising a first step in which a crystalline substance having a melting point of 70 to 220° C. consisting of a compound of formula (1):

(1)

(wherein, $R_1$, $R_2$, $R_4$ and $R_5$ represent each independently a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R_3$ each independently represents a hydrogen atom or alkyl group having 1 to 8 carbon atoms, X represents a single bond, sulfur atom or —CH($R_6$)— group (here, $R_6$ represents a hydrogen atom, alkyl group having 1 to 8 carbon atoms or cycloalkyl group having 5 to 8 carbon atoms), A represents an alkylene group having 2 to 8 carbon atoms or *—$COR_7$— group ($R_7$ represents a single bond or alkylene group having 1 to 8 carbon atoms, and * represents bonding to the oxygen side), either one of Y and Z represents a hydroxyl group, alkoxy group having 1 to 8 carbon atoms or aralkyloxy group having 7 to 12 carbon atoms, and another one represents a hydrogen atom or alkyl group having 1 to 8 carbon atoms);

is melted by heating at a temperature of not lower than the melting point, and a second step in which the melted substance obtained in the first step is cooled and solidified.

2. The method according to claim 1, wherein in the formula (1), $R_1$, $R_2$ and $R_4$ represent a t-butyl group, $R_3$ represents a hydrogen atom, $R_5$ represents a methyl group, X represents a single bond, A represents a propylene group, Y represents a hydroxyl group and Z represents a hydrogen atom.

* * * * *